US011325894B2

United States Patent
Tiitta et al.

(10) Patent No.: US 11,325,894 B2
(45) Date of Patent: May 10, 2022

(54) UPGRADING KETOACID

(71) Applicant: Neste Oyj, Espoo (FI)

(72) Inventors: Marja Tiitta, Porvoo (FI); Marina Linblad, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/474,852

(22) PCT Filed: Dec. 28, 2017

(86) PCT No.: PCT/EP2017/084697
§ 371 (c)(1),
(2) Date: Jun. 28, 2019

(87) PCT Pub. No.: WO2018/122296
PCT Pub. Date: Jul. 5, 2018

(65) Prior Publication Data
US 2019/0345124 A1 Nov. 14, 2019

(30) Foreign Application Priority Data

Dec. 30, 2016 (EP) .................................... 16207465

(51) Int. Cl.
*C07D 307/33* (2006.01)
*B01J 29/70* (2006.01)
*B01J 29/80* (2006.01)
*C10G 45/12* (2006.01)
*C10L 1/04* (2006.01)
*B01J 29/06* (2006.01)

(52) U.S. Cl.
CPC ............ *C07D 307/33* (2013.01); *B01J 29/70* (2013.01); *B01J 29/7007* (2013.01); *B01J 29/80* (2013.01); *C10G 45/12* (2013.01); *C10L 1/04* (2013.01); *B01J 2029/062* (2013.01); *C10G 2300/1014* (2013.01); *C10L 2200/0484* (2013.01)

(58) Field of Classification Search
CPC ..... C07D 307/33; B01J 29/70; B01J 29/7007; B01J 29/80; B01J 2029/062; C10G 45/12; C10G 2300/1014; C10L 1/04; C10L 2200/0484
USPC ........................................................ 562/577
See application file for complete search history.

(56) References Cited

U.S. PATENT DOCUMENTS

| 2006/0135793 | A1 | 6/2006 | Blessing et al. |
| 2006/0162239 | A1* | 7/2006 | Van Den Brink .... C07C 51/377 44/385 |
| 2010/0217038 | A1* | 8/2010 | Ayoub ..................... C07C 51/36 562/512 |
| 2015/0175497 | A1* | 6/2015 | Lauterbach .............. C10G 3/47 585/733 |
| 2016/0221912 | A1 | 8/2016 | Myllyoja et al. |
| 2016/0221914 | A1 | 8/2016 | Myllyoja et al. |
| 2016/0264876 | A1 | 9/2016 | Mascal et al. |
| 2017/0008864 | A1 | 1/2017 | Lindblad et al. |
| 2017/0073294 | A1 | 3/2017 | Myllyoja et al. |

FOREIGN PATENT DOCUMENTS

| CN | 101094719 A | 12/2007 | |
| CN | 106211781 A | 12/2016 | |
| WO | 2015144856 A1 | 10/2015 | |
| WO | WO-2015144993 A1 * | 10/2015 | .......... B01J 35/1014 |

OTHER PUBLICATIONS

McCusker "Zeolite Structures" Chapter 3 of Studies in Surface Science and Catalysis 137 H. van Bekkum, E.M. Flanigen, P.A. Jacobs and J.C. Jansen (Editors) 2001 Elsevier Science B.V.*
Office Action (Communication) dated Jul. 3, 2019, by the European Patent Office in corresponding European Patent Application No. 16207465.2 (6 pages).
International Search Report (PCT/ISA/210) dated Feb. 19, 2018, by the European Patent Office as the International Searching Authority for International Application No. PCT/EP2017/084697.
Written Opinion (PCT/ISA/237) dated Feb. 19, 2018, by the European Patent Office as the International Searching Authority for International Application No. PCT/EP2017/084697.
Patil, C. R., et al., "Esterification of Levulinic acid to ethyl levulinate over bimodal micro-mesoporous H/BEA zeolinte derivates", Catalysis Communications, vol. 42, Jan. 1, 2014, pp. 188-191.
European Search Report for EP 16207465.2 dated Jun. 14, 2017 (7 pages).
H. Difei et al., "Applications of Mesoporous MCM-41 in Heterogeneous Catalysis of Synthesis of Fine Chemicals", Progress in Chemistry, Mar. 2002, pp. 98-106, vol. 14, No. 2.
Office Action dated Mar. 3, 2021, by the Chinese Patent Office in corresponding Chinese Patent Application No. 201780076955.7. (11 pages).
Third Office Action dated Dec. 16, 2021, by the Chinese Patent Office in corresponding Chinese Patent Application No. 201780076955. 7, and an English Translation of the Office Action. (28 pages).

\* cited by examiner

*Primary Examiner* — Ling Siu Choi
*Assistant Examiner* — Ronald Grinsted
(74) *Attorney, Agent, or Firm* — Buchanan Ingersoll & Rooney PC

(57) ABSTRACT

The present invention relates to a method using a specific catalyst for upgrading ketoacid to intermediates for fuel and chemical industry, intermediates obtained by the method and to their use.

19 Claims, No Drawings

UPGRADING KETOACID

TECHNICAL FIELD

The present invention relates to a method for upgrading ketoacid to intermediates for fuel and chemical industry, intermediates obtained by the method and to the use of these intermediates. The method specifically related to dimerisation and/or oligomerisation of ketoacid to obtain an upgraded product (intermediate).

TECHNICAL BACKGROUND

WO 2015/144856 A1 discloses a method of upgrading ketoacid using a solid metal oxide catalyst system.

Perego et. al., Microporous and Mesoporous Materials, 144 (2011), 29-39 disclose zeolites and mesoporous materials e.g. for conversion of hydrocarbon-like materials and for transesterification reactions.

SUMMARY OF THE INVENTION

Although the prior art discloses several methods for upgrading ketoacid and these methods achieve reasonable results, there is still need for improved processes allowing better performance. Specifically, it is desired to achieve simple product control with high selectivity and high turnover even at low temperature while avoiding rapid deactivation of the catalyst system.

The present invention is defined in the independent claims. Further beneficial embodiments are set forth in the dependent claims. Specifically, the present invention relates to one or more of the following items:

1. A method for producing intermediate suitable for production of fuel and/or chemicals, the method comprising providing a feedstock comprising at least one ketoacid, wherein a ketoacid has a carbonyl-functional group and a carboxylic acid functional group, wherein the carbonyl-functional group may be a keto-functional or an aldehyde-functional group and the carboxylic acid may be a free acid or an acid derivative, and dimerising and/or oligomerising the at least one ketoacid in the feedstock in the presence of a heterogeneous catalyst to obtain a dimer/oligomer product, wherein the heterogeneous catalyst comprises an acidic zeolite embedded in a mesoporous matrix.

2. The method according to item 1, wherein the step of dimerising/oligomerising is a step of oligomerising the at least one ketoacid in the feedstock in the presence of the heterogeneous catalyst to obtain an oligomer product which comprises at least oligomers and optionally comprises other reaction products, such as dimers, and/or un-reacted compounds, such as monomers.

3. The method according to item 1 or 2, wherein the step of dimerising/oligomerising is carried out such that no other reactions, such as hydrogenation, take place significantly.

4. The method according to any one of items 1 to 3, wherein no metal is supported on the catalyst.

5. The method according to any one of items 1 to 4, wherein no metal is supported on the zeolite.

6. The method according to any one of items 1 to 4, wherein no metal having hydrogenating activity is supported on the catalyst 7. The method according to any one of items 1 to 6, wherein the feedstock comprises at least one γ-ketoacid.

8. The method according to item 7, wherein the feedstock further comprises ketoacid(s) other than γ-ketoacid(s).

9. The method according to any one of items 1 to 7, wherein the feedstock comprises γ-ketoacid(s) as the only ketoacid(s).

10. The method according to any one of items 1 to 9, wherein the feedstock comprises at least levulinic acid (LA).

11. The method according to any one of items 1 to 10, wherein the dimerisation/oligomerisation in the step of dimerising/oligomerising proceeds through a C—C-coupling reaction.

12. The method according to any one of items 1 to 11, wherein the content of levulinic acid in the feedstock relative to all ketoacids in the feedstock is at least 20 wt.-%, preferably at least 25 wt.-%, at least 30 wt.-%, at least 35 wt.-%, at least 40 wt.-%, at least 45 wt.-%, at least 50 wt.-%, at least 55 wt.-%, at least 60 wt.-%, at least 65 wt.-%, at least 70 wt.-%, at least 75 wt.-%, at least 80 wt.-%, at least 85 wt.-%, at least 90 wt.-%, at least 95 wt.-%, at least 97 wt.-%, or at least 99 wt.-%.

13. The method according to any one of items 1 to 12, wherein the content of the at least one ketoacid in the feedstock is at least 20 wt.-%, preferably at least 30 wt.-%, at least 35 wt.-%, at least 40 wt.-%, at least 45 wt.-%, at least 50 wt.-%, at least 55 wt.-%, at least 60 wt.-%, at least 65 wt.-%, at least 70 wt.-%, at least 75 wt.-%, at least 80 wt.-%, at least 85 wt.-%, at least 90 wt.-%, at least 95 wt.-%, at least 97 wt.-%, or at least 98 wt.-%.

14. The method according to any one of items 1 to 13, wherein the step of dimerising/oligomerising is carried out at a reaction temperature in the range of 120° C. to 250° C., wherein the reaction temperature is preferably 125° C. or more, 130° C. or more, 140° C. or more, 145° C. or more, 145° C. or more, or 150° C. or more. Further, the reaction temperature is preferably 245° C. or less, 240° C. or less, 230° C. or less, 220° C. or less, 215° C. or less or 210° C. or less, wherein, in an embodiment the reaction temperature may be in the range of 150° C. to 250° C., wherein specifically when dimerising/oligomerising LA (the feedstock contains at least 50 wt.-% LA relative to all carbonyl-group containing materials) the reaction temperature may be in the range of 175° C. to 225° C.

15. The method according to any one of items 1 to 14, wherein the step of dimerising/oligomerising is carried out at a WHSV (g feedstock/g catalyst/hour) [h$^{-1}$] of 0.05 or more, 0.10 or more, 0.15 or more, 0.18 or more, 0.20 or more, or 0.22 or more, and preferably 10.00 or less, ore preferably 5.00 or less, 4.00 or less, 3.00 or less, 2.50 or less, 2.00 or less, 1.50 or less, 1.30 or less, 1.00 or less, 0.80 or less, 0.60 or less, 0.50 or less, or 0.40 or less.

16. The method according to any one of items 1 to 15, wherein the step of dimerising/oligomerising is carried out at a pressure (absolute) of 0.5 to 50 bar, preferably 0.5 bar or more, 0.6 bar or more, 0.8 bar or more, 0.9 bar or more, or 1.0 bar or more, preferably 50.0 bar or less, 40.0 bar or less, 35.0 bar or less, 30.0 bar or less, 25.0 bar or less, 22.0 bar or less, or 20.0 bar or less, specifically preferably at a pressure (absolute) in the range of 0.5 to 20 bar.

17. The method according to any one of items 1 to 16, wherein the step of dimerising/oligomerising is carried in the presence of a carrier gas.

18. The method according to any one of items 1 to 17, wherein the feedstock comprises a solvent.

19. The method according to any one of items 1 to 18, further comprising a hydrogenation step of hydrogenating the intermediate dimer/oligomer product to obtain a hydrogenated dimer/oligomer product.

20. The method according to any one of items 1 to 19, wherein the feedstock comprises ketone(s) (including aldehyde(s)) and the step of dimerising and/or oligomerising results in mixed dimer(s) and/or mixed oligomer(s) of ketoacid and ketone, wherein the ketone(s) is (are) no ketoacid(s). The content of the ketone(s) is preferably 0 to 70 wt.-%, preferably at least 5 wt.-%, at least 10 wt.-%, at least 15 wt.-%, at least 20 wt.-%, at least 25 wt.-%, at least 30 wt.-%, or at least 35 wt.-% relative to the sum of the ketoacid(s) and ketone(s) being 100 wt.-%, preferably 65 wt.-% or less, 60 wt.-% or less, 55 wt.-% or less, or 55 wt.-% or less relative to the sum of the ketoacid(s) and ketone(s) being 100 wt.-%.

21. The method according to any one of items 1 to 20, wherein the acidic zeolite embedded in a mesoporous matrix has specific surface area in the range of 400-1400 $m^2/g$, preferably 500-1200 $m^2/g$.

22. The method according to any one of items 1 to 21, wherein the acidic zeolite embedded in a mesoporous matrix comprises a mesoporous matrix selected from M41S group, preferably a mesoporous matrix selected from MCM-41 or MCM-48.

23. The method according to any one of items 1 to 22, wherein the acidic zeolite embedded in a mesoporous matrix comprises a MCM-41 mesoporous matrix.

24. The method according to any one of items 1 to 23, wherein the acidic zeolite embedded in a mesoporous matrix comprises a MCM-48 mesoporous matrix.

25. The method according to any one of items 1 to 24, wherein the acidic zeolite embedded in a mesoporous matrix comprises a medium pore zeolite selected from MFI, MU, TON, AEF, MWW and FER zeolites or a large pore zeolite selected from BEA, FAU, MOR zeolites, preferably the zeolite is MFI, MU, AEF, BEA, MWW or MOR zeolite.

26. The method according to any one of items 21 to 25, wherein the mesoporous matrix is MCM-41 or MCM-48 and the zeolite is MFI or BEA or MWW or MOR zeolite.

27. The method according to any one of items 1 to 26, wherein the heterogeneous catalyst is in proton form or cationic.

28. The method according to any one of items 1 to 27, wherein the heterogeneous catalyst comprises 90-10 wt.-% of the acidic zeolite embedded in a mesoporous matrix and 10-90 wt.-% of a carrier.

29. The method according to any one of items 1 to 28, wherein content of oligomers is 20 wt.-% or more, preferably 25 wt.-% or more, 30 wt.-% or more, 35 wt.-% or more, 40 wt.-% or more, 45 wt.-% or more, 50 wt.-% or more, 55 wt.-% or more, 60 wt.-% or more, 65 wt.-% or more, 70 wt.-% or more, 75 wt.-% or more, or 80% or more relative to the sum of dimers and oligomers in the dimer/oligomer product.

30. A use of the hydrogenated dimer/oligomer product obtainable by the method according to item 19 as a fuel component.

31. The use of according to item 30, wherein the hydrogenated dimer/oligomer product is used as a fuel component of diesel fuel.

32. The use of according to item 30, wherein the hydrogenated dimer/oligomer product is used as a fuel component of aviation fuel (jet fuel).

33. A use of a heterogeneous catalyst comprising an acidic zeolite embedded in a mesoporous matrix for dimerising and/or oligomerising a ketoacid or a mixture of ketoacids.

34. The use according to item 33 in a method as defined in any one of items 1 to 29.

35. A use of the intermediate obtainable by the method according to any one of items 1 to 29 as a renewable raw material in chemical industry.

36. The use of according to item 35, wherein the intermediate is used as a renewable raw material in polymer production.

37. The use of according to item 35, wherein the intermediate is used as a renewable raw material in the production of fine chemicals.

DETAILED DESCRIPTION OF THE INVENTION

The invention is now explained in detail with reference to specific embodiments. It is to be noted that any feature of the embodiments may be combined with any feature of another embodiment provided that such a combination does not result in a contradiction.

The method for producing intermediate according to the present invention comprises a preparation step of providing a feedstock comprising at least one ketoacid, and a step of dimerising and/or oligomerising the at least one ketoacid in the feedstock in the presence of a heterogeneous catalyst to obtain a dimer/oligomer product (dimerisation/oligomerisation step). The heterogeneous catalyst of the present invention comprises an acidic zeolite embedded in a mesoporous matrix.

Feedstock

The feedstock in the method of the present invention comprises at least one ketoacid. Ketoacids are organic molecules that have both a carbonyl (keto) functional group (>C=O) as well as a carboxylic acid functional group. The carboxylic acid may be present as a free acid (COOH) or in the form of an acid derivative, such as a carboxylate (COO$^-$), an ester or an anhydride. The ester may be alkyl ester including branched and cyclic and substituted alkyl. Further, in the present invention, ketoacids include embodiments where the carbonyl function is an aldehyde (—CH=O) function.

In the present invention, the ketoacid may for example be an α-ketoacid (such as pyruvic acid, oxaloacetic acid and α-ketoglutaric acid), β-ketoacid (such as acetoacetic acid), γ-ketoacid (such as levulinic acid), or δ-ketoacid. The ketoacid may have more than one keto (carbonyl) functionality, and more than one carboxylic acid function. Preferably, the ketoacid only has (exactly) one keto (carbonyl) functionality and (exactly) one carboxylic acid functionality. Scheme 1 illustrates exemplary ketoacids having one keto functionality and one carboxylic acid functionality.

Scheme 1

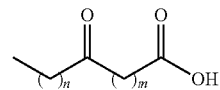

The at least one ketoacid may be a ketoacid according to scheme 1 where n and m are each independently an integer of 0, 1, 2, 3, 4, 5, 6, 7, 8, 9, or 10. Preferably, the feedstock comprises at least a γ-ketoacid (m=2). Particularly preferably, the feedstock comprises at least levulinic acid (m=2, n=0). The feedstock may contain (exactly) one ketoacid or may contain the at least one ketoacid in addition to other ketoacids.

If more than one ketoacid is present in the feedstock, it is preferable that at least one, preferably each thereof is represented by scheme 1 above (wherein m and n are each independently an integer in the range of from 0 to 10). If the feedstock contains more than one ketoacid, the dimer/oligomer product may be a mixed dimer and/or mixed oligomer formed from at least two different ketoacids. Preferably at least one of the more than one ketoacids is a γ-ketoacid.

While the method of present invention works with any of the ketoacids described above, it is preferable that the feedstock contains at least levulinic acid. Specifically, levulinic acid is readily available in large amounts from biomass. Moreover, levulinic acid shows good reactivity and the product distribution obtained by oligomerising/dimerising levulinic acid is favourable for use in many fields, such as fuel industry and chemical industry.

When the feedstock comprises at least levulinic acid, the content of levulinic acid in the feedstock relative to all ketoacids in the feedstock is preferably at least 20 wt.-%. The content may be at least 25 wt.-%, at least 30 wt.-%, at least 35 wt.-%, at least 40 wt.-%, at least 45 wt.-%, at least 50 wt.-%, at least 55 wt.-%, at least 60 wt.-%, at least 65 wt.-%, at least 70 wt.-%, at least 75 wt.-%, at least 80 wt.-%, at least 85 wt.-%, at least 90 wt.-%, at least 95 wt.-%, at least 97 wt.-%, or at least 99 wt.-%.

The content of the at least one ketoacid in the feedstock i.e. relative to the feedstock as a whole may be at least 20 wt.-%, preferably at least 30 wt.-%, at least 35 wt.-%, at least 40 wt.-%, at least 45 wt.-%, at least 50 wt.-%, at least 55 wt.-%, at least 60 wt.-%, at least 65 wt.-%, at least 70 wt.-%, at least 75 wt.-%, at least 80 wt.-%, at least 85 wt.-%, at least 90 wt.-%, at least 95 wt.-%, at least 97 wt.-%, or at least 98 wt.-%. The rest of the feedstock may be a material other than a ketoacid. It is to be noted that the catalyst is not regarded as being part of the feedstock. The feedstock may further comprise a ketone or more than one ketones. In this case, the step of dimerising and/or oligomerising may result in mixed dimer(s) and/or mixed oligomer(s) of ketoacid(s) and ketone(s). In this context, the ketone is a compound having a carbonyl-group (C═O) and thus includes ketone(s) and aldehyde(s) but having no acid functionality in addition to the carbonyl-group (preferably no acid functionality at all). In other words, the ketone is no ketoacid.

The feedstock may comprise a solvent. The solvent in the present invention is a solvent which is suited to dissolve at least one of the reactants in the dimerisation/oligomerisation step, preferably at least one ketoacid. The solvent may be present in the feedstock (relative to the feedstock as a whole) preferably in an amount of 60 wt.-% or less, 50 wt.-% or less, 40 wt.-% or less, 35 wt.-% or less, 30 wt.-% or less, 25 wt.-% or less, 20 wt.-% or less, 15 wt.-% or less, 10 wt.-% or less, or 5 wt.-% or less. Since the presence of a solvent is not required for carrying out the reaction, it is possible that no solvent is present (0 wt.-%). In any case, the solvent is a compound which does not react with the ketoacid under the conditions of the dimerisation/oligomerisation reaction.

Dimerisation/Oligomerisation Step

In the present invention the at least one ketoacid is dimerised and/or oligomerised.

Although it is not desired to be bound to theory, it is thought that the dimerisation/oligomerisation proceeds through aldol-condensation or ketonisation-type C—C-coupling reaction(s). Anyways, many C—C-coupling reactions are known in the art, and the skilled person would be able to identify such C—C-coupling reactions based on the reaction conditions provided. In particular the C—C-coupling reactions may be reactions proceeding through an enol or enolate intermediate.

In the present invention, the dimerisation/oligomerisation is preferably an oligomerisation. That is, the reaction results in the formation of at least oligomers. In the context of the present invention, oligomers are trimers or higher, specifically trimers, tetramers, pentamers or hexamers, preferably mainly (more than 50 wt.-% relative to all oligomers) trimers and tetramers. The oligomers may be homooligomers (constituted of one type of ketoacid) or heterooligomers/mixed oligomers (constituted of different types of reactants, e.g. two different ketoacids or three different ketoacids). In the case of mixed oligomers, the oligomer product may contain a mixture of different mixed oligomers. Specifically, the content of oligomers is preferably 20 wt.-% or more, more preferably 25 wt.-% or more, 30 wt.-% or more, 35 wt.-% or more, 40 wt.-% or more, 45 wt.-% or more, 50 wt.-% or more, 55 wt.-% or more, 60 wt.-% or more, 65 wt.-% or more, 70 wt.-% or more, 75 wt.-% or more, or 80% or more relative to the sum of dimers and oligomers in the dimer/oligomer product. Since oligomers are a favourable product fraction, it is preferably that the content thereof in the product (dimer/oligomer product) is high. Unlike conventional methods, the method of the present invention is suited to achieve high relative amounts of oligomers, even at moderate temperature. Thus, the present method can produce oligomers while reducing the risk of side reactions, such as coke formation.

Preferably, the step of dimerising/oligomerising is carried out such that no other reactions take place significantly. Being "carried out such that no other reactions take place significantly" means that the reaction conditions and reactants/catalyst are selected such that the dimerisation/oligomerisation is promoted and no other reaction is actively promoted.

For example, it is particularly preferable that no hydrogenation is carried out in the dimerisation/oligomerisation step. That is, the dimerisation/oligomerisation reaction works well without hydrogenation. However a small degree of hydrogenation is not harmful for the reaction. If, on the other hand, hydrogenation is used a lot, the production of oligomers is decreased and the most common reaction products would be dimers. Accordingly, especially when focussing on oligomer production, it is preferable that the reaction conditions are selected such that no hydrogenation reaction is actively promoted. This means that the reaction conditions specifically avoid the combined presence of a hydrogenation catalyst and hydrogen gas.

This can be achieved by various means. For example, it is possible that no metal having hydrogenating activity is supported on the zeolite of the catalyst. Similarly, it is possible that no metal is supported on the zeolite and/or on the catalyst.

By avoiding side-reactions (including hydrogenation), the dimerisation/oligomerisation reaction can proceed smoothly, predictable and in high conversion with high selectivity.

The step of dimerising/oligomerising may be carried out under any suitable conditions of temperature, pressure, WHSV (or ratio feedstock/catalyst), etc. and may be carried out in a flow type reactor or in a batch type reactor.

Suitable temperature conditions include e.g. a reaction temperature in the range of 120° C. to 250° C. The reaction temperature is preferably 125° C. or more, 130° C. or more, 140° C. or more, 145° C. or more, 145° C. or more, or 150° C. or more. Further, the reaction temperature is preferably 245° C. or less, 240° C. or less, 230° C. or less, 220° C. or less, 215° C. or less or 210° C. or less. In an embodiment the reaction temperature may be in the range of 150° C. to 250° C. Specifically, when dimerising/oligomerising LA the reaction temperature may be in the range of 175° C. to 225° C.

The WHSV [1/h] may preferably be 0.05 or more, 0.10 or more, 0.15 or more, 0.18 or more, 0.20 or more, or 0.22 or more, and preferably 10.00 or less, ore preferably 5.00 or less, 4.00 or less, 3.00 or less, 2.50 or less, 2.00 or less, 1.50 or less, 1.30 or less, 1.00 or less, 0.80 or less, 0.60 or less, 0.50 or less, or 0.40 or less.

Suitably, the step of dimerising/oligomerising may be carried out at a pressure (absolute) of 0.5 to 50 bar, preferably 0.5 bar or more, 0.6 bar or more, 0.8 bar or more, 0.9 bar or more, or 1.0 bar or more, preferably 50.0 bar or less, 40.0 bar or less, 35.0 bar or less, 30.0 bar or less, 25.0 bar or less, 22.0 bar or less, or 20.0 bar or less, specifically preferably at a pressure (absolute) in the range of 0.5 to 20 bar.

The step of dimerising/oligomerising may carried in the presence of a carrier gas. The carrier gas is not part of the feedstock. The carrier gas may be nitrogen gas, argon gas, helium gas or another of the noble gases, carbon dioxide gas, or gas behaving inertly to the reaction conditions of the present invention or mixtures thereof, for example. The carrier gas can be used to expel gaseous or volatile reaction products and is thus suited to shift the reaction to the product side. Thus, the presence of carrier gas is preferable. Nevertheless, it is possible that no carrier gas is used.

The dimerisation/oligomerisation step results in a dimer and/or oligomer product. This dimer/oligomer product may be directly used as the intermediate of the present invention or may be purified and/or further processed to give the intermediate of the present invention. Depending on the actual use conditions, a purification of the dimer/oligomer product may be desirable. Specifically, if mixed oligomers is produced (which usually results in the formation of multiple different mixed oligomers), it is desirable to purify the resulting product (i.e. to separate the respective types of oligomers) when the intended use is e.g. the production of fine chemicals. When producing fuels on the other hand, the mixtures may be subjected to hydrogenation without preceding purification/separation, since fuels are usually composed of mixtures of compounds.

Heterogeneous Catalyst

The heterogeneous catalyst of the present invention comprises an acidic zeolite embedded in a mesoporous matrix.

The catalyst of the present invention shows exceptionally high reactivity together with exceptionally high stability, specifically hydrothermal stability. Further, unlike conventional catalysts, such as IER (ion exchange resin) catalysts, the catalyst of the present invention is suited to promote the oligomerisation of ketoacid(s) at low temperature whereas Pd-IER (Pd supported on IER) catalysts usually promote only dimerisation reaction of ketoacid(s).

A catalyst as employed in the present invention was described previously in WO 2006/070073 A1, the content of which is herewith incorporated by reference in its entirety. In WO 2006/070073 A1, this catalyst was described as being particularly suitable for processing hydrocarbons (e.g. isomerisation of alkanes and oligomerisation of alkenes) at elevated temperatures. The inventors of the present invention now found that this catalyst is suited for the dimerisation/oligomerisation of ketoacid(s), i.e. that the catalyst is reactive and stable under the conditions required for such a reaction. The inventors surprisingly found that this catalyst is not only suited for such reactions, but that the catalyst actually provides better performance than any other tested catalyst.

In a catalyst as explained above, there are amorphous walls, well-ordered pores and crystallized zeolite which zeolite is chemically bonded to the mesoporous matrix.

While it is not intended to be bound to theory, it is assumed that the catalyst of the present invention provides both high reactivity and high hydrothermal stability by combining acidic zeolite material and a mesoporous matrix material. That is, while the zeolite material provides high reactivity, the mesoporous matrix material ensures sufficient access of the reactants to the zeolite material and furthermore prevents the zeolite material from being deactivated.

In the present invention, the term mesoporous material means a material having pores in the mesopore range, i.e. in the range of 2 to 50 nm. The mesoporous material preferably has pores in the range of 2 to 15 nm, more preferably in the range of 2 to 10 nm. Further, it is preferable that the pore system of the mesoporous material is regular.

The zeolite embedded in a mesoporous material (also referred to herein as a "mesoporous material embedded with a zeolite") shows exceptional hydrothermal stability. Accordingly, the catalyst is not degraded by the water generated in the course of the dimerisation/oligomerisation reaction even under the elevated temperatures used in this reaction. This surprising property was not recognized in WO 2006/070073 A1, since water is usually not present in isomerisation reactions of alkanes. The mesoporous material is preferably a mesoporous molecular sieve.

The mesoporous material preferably comprises a mesoporous matrix selected from M41S group and comprises mesoporous materials with ordered pore system. M41S (a family of ordered, mesoporous matrices disclosed e.g. in U.S. Pat. No. 5,198,203 A) is a group of mesoporous matrix materials formed in an aqueous solution with silica and alumina precursors with $C_iH_{2i}(CH_3)N^+$— cations (i>7) at hydrothermal conditions. The most well-known members of this group are hexagonal MCM-41, cubic MCM-48 and plate-like structure MCM-50. The pore size of the mesoporous matrix can be regulated between 2 and 10 nm and the composition may contain pure silica or metallosilica, e.g. Al-, V- and Ti-substituted silica. The mesoporous matrix materials of the M41S group are amorphous by nature and their pore system is ordered.

Preferably the mesoporous matrix is selected from mesoporous alumino-silicates known as the MCM-41 group.

The mesoporous material is preferably embedded with a zeolite selected from medium pore zeolites, which are 10-member ring zeolites like MFI, MU, TON, AEF, MWW and FER structures, and large pore zeolites, which are 12-member ring zeolites like BEA, FAU and MOR structures (for a detailed classification of zeolites and zeotypes, both referred to as zeolites in the present invention, refer to "Advanced Zeolite Science and Applications", 1st edition, ISBN 9780444820013, pages 329 to 331, items 1 and 2, which are herewith incorporated by reference). Examples of said zeolite groups are ZSM-5, ZSM-23, ZSM-22, SAPO-I I, MCM-22, ferrierite, beta-, Y- and X-zeolites and mordenite. Preferably, the zeolite is MFI, MTT, AEF, MWW, MOR or BEA zeolite. The zeolite embedded in a mesoporous material preferably contains 0.01-10 wt.-% of aluminium (Al).

The heterogeneous catalyst preferably comprises the zeolite embedded in a mesoporous material and also a carrier. The carrier is preferably selected from the list consisting of alumina, silica, clay and any other carrier according to the state of the art, and combinations thereof. Preferably the carrier comprises alumina or silica. The amount of the carrier may be in the range of 10-90 wt.-%, calculated on the total weight of the catalyst.

The X-ray powder diffraction pattern of the zeolite embedded in a mesoporous material preferably demonstrates mesoporous matrix and zeolite structures. The unit cell dimension of the zeolite varies with amount of Al in the catalytic material. The unit cell size decreases with the amount of Al, from 1.982 nm in a material containing 0.2 wt.-% of Al to 1.972 nm in a material containing 3.9 wt.-% of Al, when the zeolite type was MFI (the code of the material is MMS). The change in the unit cell size is opposite to the changes observed in zeolites in general.

The total number of acid sites can be measured by the capacity of the catalytic material to bind strong base molecules, such as ammonia or pyridine. The total acidity can be measured by ammonia-temperature programmed desorption (TPD) and Brønsted and Lewis acidity by pyridine-infrared spectroscopy (FTIR).

The acidity of the zeolite embedded in a mesoporous material can be tailored by the amount of Al introduced in the structure and modifying the aluminium (Al) content in the zeolite, MCM-41 and MM phases.

The mesoporous matrix embedded with a zeolite can be manufactured using the method disclosed in WO 2006/070073 A1.

The acidic zeolite embedded in a mesoporous matrix preferably has specific surface area ($N_2$ adsorption measurement) in the range of 400-1400 $m^2/g$, preferably 500-1200 $m^2/g$. The acidic zeolite embedded in a mesoporous matrix preferably comprises a mesoporous matrix selected from M41S group, preferably a mesoporous matrix selected from MCM-41 or MCM-48. Further, the acidic zeolite embedded in a mesoporous matrix preferably comprises a medium pore zeolite selected from MFI, MTT, TON, AEF, MWW and FER zeolites or a large pore zeolite selected from BEA, FAU, MOR zeolites, preferably the zeolite is MFI, MTT, AEF, BEA, MWW or MOR zeolite. The mesoporous matrix may be MCM-41 or MCM-48 and the zeolite may be MFI or BEA or MWW or MOR zeolite.

The heterogeneous catalyst may be in proton form, cationic form or modified with metal. Preferably, the heterogeneous catalyst comprises 90-10 wt.-% of the acidic zeolite embedded in a mesoporous matrix and 10-90 wt.-% of a carrier.

Hydrogenation of the Dimer/Oligomer Product

The dimer and/or oligomer product of the present invention, the product of the dimerisation/oligomerisation step, may be subjected to hydrogenation treatment to provide a hydrogenated dimer/oligomer product. This hydrogenated dimer/oligomer product may be used as the intermediate of the present invention, preferably as it is, but it may be subjected to an optional separation and/or purification treatment.

The hydrogenated dimer/oligomer product is preferably a hydrocarbon material (consisting of carbon atoms and hydrogen atoms), while it may comprise minor amounts (up to 10 wt.-%, preferably at most 5 wt.-%, at most 3 wt.-% or at most 2 wt.-%) of impurities (such as oxygenates). The hydrocarbon material may be a mixture of different hydrocarbons. The hydrocarbon material preferably comprises mainly (50 wt.-% or more, preferably 70 wt.-% or more) alkane(s), which may be linear or branched, any are preferably mainly (50 wt.-% or more, preferably 70 wt.-% or more) branched. The hydrocarbon material may be used as an aviation fuel (jet fuel) and/or as a diesel fuel.

The hydrogenation treatment may be any conventional hydrogenation treatment known in the art, such as hydrodeoxygenation (HDO) using hydrogen gas and a HDO catalyst. The hydrogenation treatment may be a 1-step, a 2-step or a multi-step (more than 2 steps) treatment.

The HDO catalyst employed in a hydrodeoxygenation step may comprise a hydrogenation metal on a support, such as for example a HDO catalyst selected from a group consisting of Pd, Pt, Ni, Co, Mo, Ru, Rh, W or any combination of these. The hydrodeoxygenation step may for example be conducted at a temperature in the range of 100-500° C. and at a pressure in the range of 10-150 bar.

Water and light gases may be separated from the HDO product with any conventional means such as distillation. After the removal of water and light gases the HDO product, hydrogenated dimer/oligomer product, may be fractionated to one or more fractions suitable for use as a component of aviation fuel, base oil or diesel components. The fractionation may be conducted by any conventional means, such as distillation. Optionally part of the product of the HDO step may be recycled and combined to the feed of the HDO reactor.

The HDO product, hydrogenated dimer/oligomer product, may further be subjected to an isomerisation treatment.

The HDO product, hydrogenated dimer/oligomer product, which is optionally further processed e.g. by distillation and/or isomerisation, may be blended with other fuel components to provide a diesel fuel blend or an aviation fuel blend.

Use

The present invention further provides the use of a heterogeneous catalyst comprising an acidic zeolite embedded in a mesoporous matrix.

Preferably, the catalyst is as defined under the heading "Heterogeneous catalyst" above. Further, the use preferably comprise using the catalyst in a method according to the present invention. In other words, it is preferably that the same catalyst, reactants and/or reaction conditions as described above are employed in the use of the present invention.

EXAMPLES

The present invention is further illustrated by way of Examples. However, it is to be noted that the invention is not intended to be limited to the exemplary embodiments presented in the Examples. The Examples used pure levulinic acid (LA) as an embodiment of the at least one ketoacid, since this material was readily available in large amount.

Example 1

LA was subjected to reaction over a catalyst comprising β-zeolite embedded in a mesoporous MCM-41 material in a flow type reactor at a temperature of 200° C., WHSV 0.5 $h^{-1}$ and a pressure of 1 bar (absolute) under flow of nitrogen. The product stream (organic fraction) was analysed by HPLC (High Performance Liquid Chromatography) and GPC (Gel Permeation Chromatography). The quantitative amount of levulinic acid (LA) and gamma-valerolactone (GVL) was determined by HPLC and the relative amount LA dimers and oligomers was obtained from GPC data. The comparison of catalyst selectivity for oligomer formation was made at similar LA conversion levels. At the conversion levels studied the amount of gas and water formation was minor and omitted when estimated the total amount of dimers and oligomers.

The product stream contained 18 wt.-% LA dimer, 15 wt.-% LA oligomer and 67 wt.-% LA (monomer).

Example 2 (Comparative)

Example 1 was repeated with the exception that Pt-Beta (Pt supported on (3-zeolite) was used as the catalyst and the pressure was increased to 20 bar (absolute). The product stream was analysed as in Example 1. The product stream contained 21 wt.-% LA dimer, 13 wt.-% GVL and 66 wt.-% LA (monomer).

Example 3 (Comparative)

Example 2 was repeated with the exception that tungsten oxide supported on zirconia (WO₃/ZrO₂) was used as the catalyst and the temperature was increased to 220° C. The product stream was analysed as in Example 1. The product stream contained 23 wt.-% LA dimer, 4 wt.-% LA oligomer and 73 wt.-% LA (monomer) as well as negligible amounts of GVL (<1 wt.-%).

Example 4 (Comparative)

Example 2 was repeated with the exception that a Pd-supporting strong cation-exchange IER catalyst (Amberlyst CH43) was used as the catalyst and the temperature was lowered to 120° C. The product stream was analysed as in Example 1. The product stream contained 32 wt.-% LA dimer, 5 wt.-% GVL and 63 wt.-% LA (monomer).

The reaction conditions and test results of Examples 1 to 4 are summarized in the following Table:

TABLE 1

| Example | Catalyst | T, ° C. | p, bar | WHSV, h⁻¹ | LA wt.-% | GVL wt.-% | Dimers wt.-% | Oligomers wt.-% |
|---|---|---|---|---|---|---|---|---|
| 1 | MM-Beta | 200 | 1 | 0.5 | 67 | 0 | 18 | 15 |
| 2 | Pt-Beta | 200 | 20 | 0.5 | 66 | 13 | 21 | 0 |
| 3 | WO₃/ZrO₂ | 220 | 20 | 0.5 | 73 | <1 | 23 | 4 |
| 4 | Pd-IER | 120 | 20 | 0.5 | 63 | 5 | 32 | 0 |

As can be seen from the above results, the method of the present invention provides high conversion rates and high oligomer selectivity even at relatively low temperature of 200° C.

The invention claimed is:

1. A method for producing an intermediate suitable for production of fuel and/or chemicals, the method comprising:
   providing a feedstock containing at least one ketoacid; and
   dimerising and oligomerising the at least one ketoacid in the feedstock in a presence of a heterogeneous catalyst to obtain a dimer and oligomer product;
   wherein the heterogeneous catalyst contains an acidic zeolite embedded in a mesoporous matrix and a carrier,
   wherein the content of oligomers is 40 wt.-% or more relative to the sum of dimers and oligomers in the dimer and oligomer product and
   wherein the step of dimerising/oligomerising is carried out at a reaction temperature of 230° C. or less.

2. The method according to claim 1, wherein the dimerising and oligomerising includes oligomerising the at least one ketoacid in the feedstock in the presence of the heterogeneous catalyst to obtain an oligomer product containing at least oligomers, wherein the oligomers are, relative to all oligomers, more than 50 wt.-% trimers or pentamers.

3. The method according to claim 1, comprising:
   performing the dimerising and oligomerising such that no other reactions occur significantly.

4. The method according to claim 1, wherein the feedstock comprises:
   at least one γ-ketoacid.

5. The method according to claim 1, wherein the feedstock comprises:
   at least levulinic acid.

6. The method according to claim 1, wherein the dimerization and oligomerisation proceeds through a C—C-coupling reaction.

7. The method according to claim 1, wherein the acidic zeolite embedded in a mesoporous matrix has specific surface area in a range of 400-1400 m²/g.

8. The method according to claim 1,
   wherein the acidic zeolite embedded in a mesoporous matrix comprises a mesoporous matrix selected from any M41S group.

9. The method according to claim 1, wherein the acidic zeolite embedded in a mesoporous matrix comprises:
   a MCM-41 mesoporous matrix.

10. The method according to claim 1, wherein the acidic zeolite embedded in a mesoporous matrix comprises:
    a MCM-48 mesoporous matrix.

11. The method according claim 1, wherein a content of levulinic acid in the feedstock relative to all ketoacids in the feedstock is selected to be at least 20 wt.-%.

12. The method according to claim 1, wherein a content of the at least one ketoacid in the feedstock is selected to be at least 20 wt.-%.

13. The method according to claim 1, comprising:
    performing the dimerising and oligomerising at a reaction temperature in a range of 120° C. to 230° C. when dimerising and/or oligomerising levulinic acid.

14. The method according to claim 1, comprising:
    hydrogenating the dimer and oligomer product to obtain a hydrogenated dimer and oligomer product.

15. The method according to claim 14, comprising:
    blending the hydrogenated dimer and oligomer product with a fuel component to provide a fuel blend.

16. The method according to claim 1, wherein the method comprises oligomerising a mixture of ketoacids.

17. The method according to claim 1, wherein the content of oligomers is 50 wt.-% or more relative to the sum of dimers and oligomers in the dimer and oligomer product.

18. The method according to claim 1, wherein the content of oligomers is 60 wt.-% or more relative to the sum of dimers and oligomers in the dimer and oligomer product.

19. The method according to claim 1, wherein the acidic zeolite is a 12-member ring zeolite selected from the group consisting of BEA, FAU, and MOR structures.

* * * * *